(12) United States Patent
Beavis et al.

(10) Patent No.: US 8,247,607 B2
(45) Date of Patent: Aug. 21, 2012

(54) CARBONYLATION PROCESS

(75) Inventors: Richard Beavis, Berkshire (GB); Sean Anthony Hennigan, Hull (GB); Michael James Muskett, Humberside (GB)

(73) Assignee: BP Chemicals Limited, Middlesex (GB)

( * ) Notice: Subject to any disclaimer, the term of this patent is extended or adjusted under 35 U.S.C. 154(b) by 689 days.

(21) Appl. No.: 12/086,430

(22) PCT Filed: Nov. 22, 2006

(86) PCT No.: PCT/GB2006/004358
§ 371 (c)(1),
(2), (4) Date: Jul. 1, 2009

(87) PCT Pub. No.: WO2007/071902
PCT Pub. Date: Jun. 28, 2007

(65) Prior Publication Data
US 2009/0299092 A1 Dec. 3, 2009

Related U.S. Application Data

(60) Provisional application No. 60/751,989, filed on Dec. 21, 2005.

(51) Int. Cl.
*C07C 51/12* (2006.01)
(52) U.S. Cl. .................................................... 562/519
(58) Field of Classification Search .................. None
See application file for complete search history.

(56) References Cited

U.S. PATENT DOCUMENTS
6,114,576 A 9/2000 Leet et al.

FOREIGN PATENT DOCUMENTS
GB 1 261 170 1/1972
WO 2005/092829 10/2005

OTHER PUBLICATIONS
International Search Report for PCT/GB2006/004358 mailed Apr. 20, 2007.
Written Opinion for PCT/GB2006/004358 mailed Apr. 20, 2007.

*Primary Examiner* — Yevegeny Valenrod
(74) *Attorney, Agent, or Firm* — Nixon & Vanderhye

(57) ABSTRACT

Process for carbonylating an alcohol or reactive derivative thereof, by (a) feeding one or more feed streams to a reaction zone, at least one feed stream containing an alcohol or reactive derivative thereof, and at least one feed stream contains CO, (b) maintaining in the reaction zone a temperature and pressure sufficient to allow an exothermic carbonylation reaction to occur to produce a carboxylic acid or carboxylic acid anhydride, (c) removing one or more product streams containing carboxylic acid or carboxylic acid anhydride from the reaction zone, and (d) transferring heat contained in one or more product streams to a first heat-exchange stream. Heat is transferred from a second heat-exchange stream to a feed stream of step (a) before the feed stream is fed to the reaction zone, and the temperature of the second heat-exchange stream before heat transfer is lower than that of the one or more product streams.

16 Claims, 3 Drawing Sheets

CARBONYLATION PROCESS

This application is the U.S. national phase of International Application No. PCT/GB2006/004358 filed 22 Nov. 2006 which designated the U.S. and claims priority to U.S. Provisional Patent Application No. 60/751,989 filed 21 Dec. 2005, the entire contents of each of which are hereby incorporated by reference.

The present invention relates to heat transfer, more specifically to a process for capturing and reusing low-grade heat in a process for the carbonylation of an alcohol and/or reactive derivative thereof.

BACKGROUND OF THE INVENTION

Carbonylation of an alcohol and/or reactive derivative thereof to produce a carboxylic acid and/or carboxylic acid anhydride is known, as described for example in EP-A-0 144 935, EP-A-0 643 034 and U.S. Pat. No. 6,211,405.

A typical homogeneously catalysed carbonylation process entails contacting carbon monoxide with a liquid reaction composition comprising an alcohol and/or reactive derivative thereof and a group VIII carbonylation catalyst (typically rhodium and/or iridium) in a reaction zone at elevated temperature and pressure, optionally in the presence of one or more co-catalysts and/or promoters. Carboxylic acid and/or carboxylic acid anhydride is recovered from the liquid reaction composition by feeding the liquid reaction composition to a flash separation zone, wherein a liquid fraction comprising the carbonylation catalyst is returned to the reaction zone, and a vapour fraction comprising carboxylic acid and/or carboxylic acid anhydride, is fed to one or more distillation columns to separate unreacted reactants and by-products from the desired carboxylic acid and/or carboxylic acid anhydride product.

However, a problem associated with carbonylation processes is that heat can be lost from process streams whose temperature is too low to be readily and economically used elsewhere, for example whose temperature is insufficient to be transferred to a supply of pressurised steam. Such process streams are often cooled by a supply of cooling water before being sent to storage or transportation means, and so the heat is lost as waste as opposed to being captured and usefully employed.

In U.S. Pat. No. 6,114,576, an exothermic, heterogeneously catalysed carbonylation process is described in which heat from a stream withdrawn from the reactor is captured by heating process streams in the product recovery section of the process. Additionally, GB 1,261,170 describes a heat management process in the production of urea, in which heat released by condensation in a recycle stream is transferred to a reactant stream.

However, there remains a need for a carbonylation process in which heat that is otherwise lost as waste can be captured and usefully employed elsewhere, either in the same carbonylation process or in a different process.

SUMMARY OF THE INVENTION

According to the present invention there is provided a process for the carbonylation of an alcohol and/or reactive derivative thereof, which process comprises;

(a) feeding one or more reaction zone feed streams to a reaction zone, wherein at least one reaction zone feed stream comprises an alcohol and/or reactive derivative thereof, and at least one reaction zone feed stream comprises carbon monoxide;

(b) maintaining in the reaction zone a temperature and pressure sufficient to allow an exothermic carbonylation reaction to take place to produce a carboxylic acid and/or carboxylic acid anhydride;

(c) removing one or more product streams comprising carboxylic acid and/or carboxylic acid anhydride from the reaction zone;

(d) transferring heat contained in at least a portion of the one or more product streams to a first heat-exchange stream;

characterised in that heat is transferred from a second heat-exchange stream to a reaction zone feed stream of step (a) before the reaction zone feed stream is fed to the reaction zone, wherein the temperature of the second heat-exchange stream before heat transfer is lower than that of the one or more product streams.

In the carbonylation process of the present invention, one or more reaction zone feed streams are fed to a reaction zone in which an exothermic carbonylation reaction occurs to produce one or more product streams. Heat from at least a portion of the one or more product streams is fed to a first heat-exchange stream, such as a supply of pressurised steam, and which can be usefully employed elsewhere, such as in other parts of the same carbonylation process, or even in an entirely different process. At least one of the reaction zone feed streams is heated by a second heat-exchange stream, having a temperature lower than that of the one or more product streams, and which is typically a stream from which heat is generally otherwise lost as waste heat. As a consequence, the one or more product streams comprise heat originating from the second heat-exchange stream together with heat generated by the exothermic carbonylation reaction, which combined heat can be transferred to the first heat-exchange stream. Thus, heat originating from the second heat-exchange stream is transferred to the first heat-exchange stream for use elsewhere, resulting in reduced heat loss and greater process efficiency.

The second heat-exchange stream can be any stream which has a higher temperature than the reaction zone feed stream to be heated, whose temperature is too low to be usefully employed elsewhere by direct heat transfer means, and whose heat is generally lost from the process as waste heat. The temperature of the second heat-exchange stream before heat transfer is lower than the one or more product streams, and is preferably lower than the first heat-exchange stream before being heated by at least a portion of the one or more product streams.

The reaction zone feed stream that is heated by the second heat-exchange stream is any feed stream that is fed to the reaction zone and which has a temperature below that of the second heat-exchange step before heat transfer. Suitable reaction zone feed streams include a supply of fresh alcohol and/or reactive derivative thereof, a fresh supply of carbon monoxide, or a recycle stream. It is preferred that the reaction zone feed stream that is heated by the second heat-exchange stream is in the liquid phase, as the quantity of heat absorbed over a given temperature increase is generally greater than the heat absorbed by a gaseous stream over the same temperature range. The quantity of heat that can be absorbed by the reaction zone feed stream is also related to its temperature before heat transfer, thus a lower temperature reaction-zone feed stream will be able to absorb a greater quantity of heat than a higher temperature feed stream.

The reaction zone feed stream after heat transfer is fed to the reaction zone, typically with other reaction zone feed streams, such as other reactant and recycle streams. In the reaction zone, exothermic carbonylation takes place to produce one or more product streams comprising carboxylic acid and/or carboxylic acid anhydride whose temperature is higher than the reaction zone feed stream heated by the second heat-exchange stream. Preferably, the one or more product streams have a temperature higher than all the reaction zone feed streams.

At least a portion of the one or more product streams are preferably fed to a purification zone for producing purified carboxylic acid and/or anhydride, and which typically comprises one or more distillation columns. The exact nature and configuration of the purification zone will be dependent on the composition of the product stream and the operating conditions in other parts of the process, such as the reaction zone. The purification zone typically comprises one or more recycle streams, in which unreacted reactants and components that may be converted into desired products are separated from the one or more carboxylic acid and/or carboxylic acid anhydride product streams and returned to the reaction zone. The purification zone typically also comprises waste streams which are not recycled back to the reaction zone, and which comprise components that could contaminate the product. As the purified product streams and the waste streams are not recycled back to the reaction zone, and as their temperatures are typically too low for heat transfer to, for example, a supply of pressurised steam, the heat contained therein can be transferred to a reaction zone feed stream in accordance with the present invention, and hence can be the second heat-exchange stream. A stream being recycled from the purification zone to the reaction zone may also be used to heat a reaction zone feed stream if heat contained therein may otherwise be lost, for example if exothermic condensation of the contents of a gaseous recycle stream takes place. Preferably, the second heat-exchange stream is a process stream that is not recycled back to the reaction zone, preferred streams being a waste stream of the purification zone, or a purified carboxylic acid and/or carboxylic acid anhydride product stream of the purification zone. Most preferably, the second heat-exchange stream is a purified carboxylic acid and/or carboxylic acid anhydride product stream, as the volume, and hence the quantity of heat contained therein, is generally higher.

The first heat-exchange stream to which heat is transferred from at least a portion of one or more product streams may be any process stream whose temperature is initially lower than that of the one or more product streams before heat transfer, and whose temperature is preferably higher than that of the second heat-exchange stream before heat-transfer to the reaction zone feed stream.

The temperature of the one or more product streams is preferably sufficient to raise the temperature of a supply of low pressure steam, which typically has a pressure of up to 6 barg (0.7 MPa), for example about 5 to 6 barg (0.6 to 0.7 MPa) and a temperature typically of 150° C. or more. The first heat-exchange stream that is heated by at least a portion of the one or more product streams may be a supply of low pressure steam, as described above, which may in turn be used for further heat transfer purposes either within the same process or within a different process. Alternatively, the first heat-exchange stream may be a process stream within the same carbonylation process of the present invention, for example a feed stream to one or more distillation columns in the purification zone. In a further embodiment of the invention, the first-heat exchange stream may be a process stream from a different process, for example a process stream of a vinyl acetate production process which may be located near to a source of acetic acid feedstock. Preferably, the first heat-exchange stream is a supply of pressurised stream, which provides greater versatility over how the heat transferred thereto may be used. Preferably, the temperature of the one or more product streams from which heat is transferred to the first heat-exchange stream is sufficient to heat a supply of pressurised steam having a temperature of 150° C. or more.

The transfer of heat between one process stream and another is typically achieved using a heat exchanger, wherein the two streams are placed in thermal contact with each other, which results in cooling of the hotter stream, and heating of the cooler stream.

Optionally, any product stream or portion thereof that is used to transfer heat to the first heat-exchange stream is returned to the reaction zone, in which the consequently cooled product stream can assist in regulating the temperature within the reaction zone. The reaction zone temperature may be further regulated by additional cooling of the product stream before its return to the reaction zone, for example with a supply of cooling water. In a preferred embodiment of the present invention, two product streams are removed from the reaction zone. The heat from one of the product streams is transferred to the first heat-exchange stream before the consequently cooled product stream is returned to the reaction zone. The other product stream is fed to the purification zone, in which purified carboxylic acid and/or carboxylic acid anhydride is produced.

The exothermic carbonylation reaction of the present invention is preferably catalysed. This may be achieved heterogeneously or homogeneously. In a preferred embodiment of the present invention, the carbonylation reaction is catalysed by a homogeneous group VIII carbonylation catalyst, wherein a liquid reaction composition is maintained in the reaction zone, which liquid reaction composition comprises an alcohol and/or reactive derivative thereof, carboxylic acid and/or carboxylic acid anhydride, and a group VIII carbonylation catalyst.

Reactive derivatives of an alcohol include compounds that are capable of producing the alcohol as a result of a hydrolysis reaction, examples of which are alkyl carboxylates, alkyl ethers and alkyl halides. The preferred product of the carbonylation process is carboxylic acid and/or carboxylic acid anhydride. Carbonylation of alkyl carboxylate under anhydrous conditions typically results in the formation of carboxylic acid anhydride. In the presence of alcohol and/or small quantities of water, carboxylic acid is also produced. In the presence of water above a threshold concentration, typically 0.1% or more by weight in the liquid reaction composition, carboxylic acid is the predominant product.

The number of carbon atoms in the alcohol, or the alkyl group or groups of the reactive derivative of the alcohol, is one less than the number of carbons in each of the carboxylate groups of the carboxylic acid and/or carboxylic acid anhydride product. For example, acetic acid and acetic anhydride have two carbon atoms in each of their acetate groups, and there is one carbon in each of the alkyl groups of methanol and associated reactive derivatives such as methyl iodide, dimethyl ether and methyl acetate.

Water may additionally be present in the reaction zone. It may be introduced as a freshly added feed, or may alternatively or additionally be produced in the reaction zone as a result of reactions between one or more components of the liquid reaction composition, such as the condensation of alcohol with carboxylic acid to form alkyl carboxylate and water.

The present invention is particularly suitable for the carbonylation of methanol and/or reactive derivative thereof, preferable reactive derivatives of methanol being methyl acetate, dimethyl ether and methyl iodide. The preferred product is acetic acid and/or acetic anhydride. Most preferably acetic acid is the product, and therefore water is preferably present in the liquid reaction composition of the reaction zone. The concentration of water in the liquid reaction composition may vary depending on the Group VIII metal employed as catalyst Generally, for rhodium-catalysed carbonylation, water may be present in an amount in the range from 0.1 to 30%, preferably from 1 to 15% by weight. For iridium-catalysed carbonylation, water may be present in an amount from 0.1 to 10%, preferably from 1 to 6.5% by weight.

The group VIII carbonylation catalyst is preferably selected from rhodium and/or iridium, and is preferably iridium. The group VIII carbonylation catalyst may be added to the liquid reaction composition in any suitable form which dissolves in the liquid reaction composition or is convertible therein to a soluble form. Suitable compounds are described in EP-A-0 144 935, EP-A-0 643 034 and U.S. Pat. No. 6,211,405. Typically carbonyl complexes, halide salts and acetate salts of the metals may be employed. Rhodium may be present in an amount of from 50 to 5000 ppm, preferably from 100 to 1500 ppm, expressed as elemental rhodium. Iridium may be present in an amount in the range from 100 to 6000 ppm, preferably from 400 to 3000 ppm, expressed as elemental iridium.

A carbonylation catalyst promoter may also be present in the liquid reaction composition. The identity of promoter depends to some extent on the Group VIII carbonylation catalyst. When iridium is employed as the carbonylation catalyst the optional promoter is suitably a metal selected from the group consisting of ruthenium, osmium, cadmium, rhenium, mercury, gallium, indium, tungsten, and mixtures thereof, preferably ruthenium or osmium. Suitably the molar ratio of promoter:iridium is in the range [0.5 to 15]:1. When rhodium is employed as the carbonylation catalyst the optional promoter is suitably selected from the group consisting of iodide salts of alkali and alkaline earth metals, for example lithium iodide, quaternary ammonium iodides, and quaternary phosphonium iodides. Suitably the optional promoter may be present up to its limit of solubility.

An alkyl halide co-catalyst may be present in the liquid reaction composition, the halogen element preferably being iodide. In the carbonylation of methanol and/or reactive derivative thereof, methyl iodide is preferably present in the liquid reaction composition in an amount in the range from 2 to 20%, preferably from 4 to 16% by weight.

One or more compounds that are capable of producing ionic iodide in the liquid reaction composition may also be present in the liquid reaction composition, particularly for rhodium-catalysed processes in which they can act as a catalyst stabiliser. Suitable compounds include iodide salts of alkali or alkaline earth metals, or iodide salts of quaternary ammonium or phosphonium ions. Preferably, the iodide salt is an alkali metal iodide, most preferably lithium iodide. Ionic iodide-generating compounds are preferably avoided for iridium catalysed processes, as they may inhibit the reaction.

Alkyl carboxylate may also be present in the liquid reaction composition, either being introduced to the carbonylation reactor as a reactant, or being formed by the reaction of an alcohol and/or reactive derivative thereof with carboxylic acid or carboxylic acid anhydride. In the carbonylation of methanol and/or reactive derivative thereof, methyl acetate will be present in the liquid reaction composition. For an iridium-catalysed process, methyl acetate will preferably be present at a concentration of from 1 to 70 wt %, more preferably 2 to 50 wt %, and most preferably from 5 to 40 wt %. For a rhodium-catalysed process, the methyl acetate concentration is preferably from 2 to 15 wt %, more preferably from 3 to 10 wt %.

Carbon monoxide is present in the reaction zone at a preferable partial pressure of from 2.5 to 100 bar (0.25 to 10 MPa), more preferably 3 to 20 bar (0.3 to 2 MPa). The carbon monoxide may be essentially pure or may contain inert impurities such as carbon dioxide, methane, nitrogen, noble gases, water, and $C_1$ to $C_4$ paraffinic hydrocarbons. The presence of hydrogen in the carbon monoxide feed and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than 1 bar (0.1 MPa) partial pressure, more preferably less than 0.5 bar (50 kPa) and yet more preferably less than 0.3 bar (30 kPa). The partial pressure of carbon monoxide in the reactor is suitably in the range greater than 0 to 40 bar (0 to 4 MPa), typically from 4 to 30 bar (0.4 to 3 MPa).

The reaction zone feed stream that is heated by the second heat-exchange stream may be, for example, a fresh source of alcohol and/or reactive derivative thereof, a fresh supply of catalyst, or a recycle stream from other parts of the process, such as a recycle stream of recyclable components from the purification zone to the reaction zone. The reaction zone feed stream, before heat transfer, will have a lower temperature than the second heat-exchange stream. Typically, the temperature of the reaction zone feed stream is 80° C. or below, more preferably 60° C. or below, and most preferably 40° C. or below. After heat exchange, the temperature of the reaction zone feed stream is preferably greater than 40° C., preferably greater than 60° C., and most preferably greater than 80° C. Preferably, the reaction zone feed stream is an alcohol, more preferably an alcohol in the liquid phase.

Preferably the reaction zone in which the exothermic carbonylation reaction occurs is maintained at a temperature and pressure sufficient to ensure that exothermic carbonylation is maintained. Typically, the temperature will be from 100 to 300° C., more preferably from 170 to 220° C. A pressure of from 17 to 100 bara (1.7 to 10.0 MPa) is typically maintained within the reaction zone, preferably from 20 to 80 bara (2.0 to 8.0 MPa), more preferably from 20 to 40 bara (2.0 to 4.0 MPa).

In a preferred embodiment of the invention, liquid reaction composition is withdrawn from the reaction zone to form at least two product streams. Heat within one of the product streams is transferred to the first heat-exchange stream before being fed back to the reaction zone, optionally with further cooling. The temperature of the liquid reaction composition is controlled by controlling the quantity of heat transferred to the first heat-exchange stream. Thus, more heat is transferred to the first heat-exchange stream when hotter reactants are introduced to the reaction zone in order to regulate the temperature in the liquid reaction composition withdrawn from the reaction zone. Optional further cooling may be carried out after the heat-transfer step in order to provide additional control over the temperature within the reaction zone. In yet a further embodiment, product stream that is recycled-back to the reaction zone is first fed to a second reaction zone before heat-transfer to the first heat-exchange stream. The second reaction zone allows further reaction of entrained and/or dissolved carbon monoxide, which further raises the temperature of the product stream, allowing yet more heat to be transferred to the first heat-exchange stream. In this embodiment of the invention, another of the at least two product streams is fed to the purification zone, and is optionally first fed to a second reaction zone so that carbon monoxide dissolved and/or entrained therein may further react to form additional carbonylation product.

In the present invention, at least a portion of the one or more product streams are fed to a purification zone, which produces purified carboxylic acid and/or carboxylic acid anhydride. The purification zone will typically comprise a flash separation zone and a distillation zone.

In a preferred embodiment of the present invention, in which the carbonylation reaction is homogeneously catalysed, any product stream or portion thereof that is fed to the purification zone is separated into a vapour fraction and a liquid fraction in the flash separation zone. The liquid fraction comprises the relatively involatile components, such as group VIII carbonylation catalyst and any metallic promoters and/or ionic iodide promoters that may optionally be present. The liquid fraction is recycled to the reaction zone, optionally with prior cooling to regulate the temperature within the reaction zone.

The vapour fraction of the flash separation zone comprises relatively volatile components, such as unreacted alcohol and/or reactive derivative thereof, carboxylic acid and/or anhydride product, and other volatile components such as water and alkyl iodide.

The vapour fraction is fed to the distillation zone, which comprises one or more distillation columns that purify the carboxylic acid and/or carboxylic acid anhydride product by removing impurities and by-products to produce a purified product stream.

The purification zone typically comprises recycle streams, which comprise components such as unreacted reactants, water or components that may be returned to the reaction zone where they can react to form desired products of the reaction. As the heat contained in such recycle streams is returned to the reactor, they are typically not used to transfer heat to the reaction zone feed stream. However, where heat can be lost from a recycle stream, for example through exothermic processes such as condensation, then the heat can be usefully captured in accordance with the present invention by being transferred to a different reaction zone feed stream.

In preferred embodiments of the invention, heat from one or more waste streams and/or purified product streams of the purification zone is transferred to one or more reaction zone feed streams, as the heat in such streams would otherwise be lost from the process unless captured.

In one embodiment of the invention, methanol and/or reactive derivative thereof is carbonylated to produce acetic acid, wherein the distillation zone comprises three distillation columns, as described for example in Howard et al, Catalysis Today, 18 (1993), pp. 325-354. The more volatile components, or light ends, are removed from the head of the first distillation column, and preferably, at least in part, recycled to the reactor. The light ends typically comprise methyl acetate, unreacted methanol, methyl iodide, and some of the water. Optionally, from the base of the first distillation column, a stream comprising entrained carbonylation metal catalyst and/or promoter is returned to the reaction zone. A side stream, comprising acetic acid product and water is fed to a second distillation column, wherein water is removed from the head of the column, where it is preferably recycled at least in part to the reaction zone. A substantially dry acetic acid stream is removed from the second column and fed to the third distillation column, wherein heavier impurities, such as propionic acid, are removed and disposed of, to leave purified acetic acid. Substantially dry acetic acid typically has a water concentration of 0.5 wt % or below, preferably 0.2% or below, and most preferably 0.1 wt % or below.

In an alternative embodiment of the invention, relating to the production of acetic acid from carbonylation of methanol and/or reactive derivative thereof, the distillation zone comprises two distillation columns, as described in EP-A-0 849 250, the first distillation column being a combined light ends removal and drying column.

In a further embodiment of the invention, wherein methanol undergoes carbonylation to produce acetic, there is only a single distillation column in the distillation zone, as described in EP-A-0 573 189. Thus, light ends, heavy impurities and water are all removed from the acetic acid product in a single distillation column.

In yet another embodiment of the present invention, acetic acid and acetic anhydride are co-produced by carbonylation of methyl acetate, as described for example in the aforementioned "Catalysis Today" article by Howard et al. The distillation zone comprises a first distillation column for removing light ends from the vapour fraction of the flash separation zone. Acetic acid and acetic anhydride are separated in a second distillation column, the acid/anhydride separation column, wherein the acetic acid is removed from the upper portion of the column, and the anhydride from the lower portion. The acetic acid is transferred to a third distillation column, where further light ends are removed from the head of the column and optionally recycled, at least in part, back to the reactor. The light ends, which may comprise some water and methyl iodide, may optionally be used to esterify any acetic acid therewith to methyl acetate, in order to control the ratio of acetic acid to acetic anhydride produced by the process. Purified acetic acid is extracted as a side-stream from a final polishing column. Acetic anhydride is fed from the acid/anhydride separation column to a further distillation column, wherein heavy impurities, such as ethylidene diacetate, are removed from the base of the column. Acetic anhydride is removed as a side-stream from an upper portion of the column and fed to a final flashing column to remove residual lighter impurities.

Light ends removed from the product stream in the purification zone may be suitable for being recycled to the reaction zone, as they typically contain components such as methyl iodide, methyl acetate, water and methanol, which can be reused to make further acetic acid and/or acetic anhydride. The heat within these recycled streams is therefore returned to the reaction zone, and so heat contained therein is generally not lost from the process, and so does not need to be transferred to a reaction zone feed stream.

Heavier components, such as propionic acid or ethylidene diacetate, are removed from the process as waste streams, and heat within these waste streams is therefore potentially lost from the process. Therefore, such waste streams may be used as the second heat-exchange stream, for transferring heat to a reaction zone feed stream to prevent or reduce the quantity of heat lost from the process.

The purified acetic acid and/or acetic anhydride streams will also comprise heat that may be lost from the process, as purified product is generally not recycled back to the reaction zone. Thus, the purified acetic acid and/or acetic anhydride streams are also suitably employed as the second heat-exchange stream for transferring heat contained therein to a reaction zone feed stream in order to reduce heat loss from the process.

Thus, in a preferred embodiment of the present invention, the second heat-exchange stream is a waste stream comprising heavy impurities from the purification zone, or a purified product stream comprising purified acetic acid and/or acetic anhydride. Most preferably, a purified acetic acid and/or acetic acid anhydride product stream is the second heat-exchange stream, as the volume of material is generally higher than the volume of waste streams from the purification zone.

BRIEF DESCRIPTION OF THE DRAWINGS

The process of the present invention will now be illustrated by the following non-limiting examples, with reference to FIGS. 1, 2 and 3, where.

DETAILED DESCRIPTION OF PREFERRED EMBODIMENTS

Figure 1:
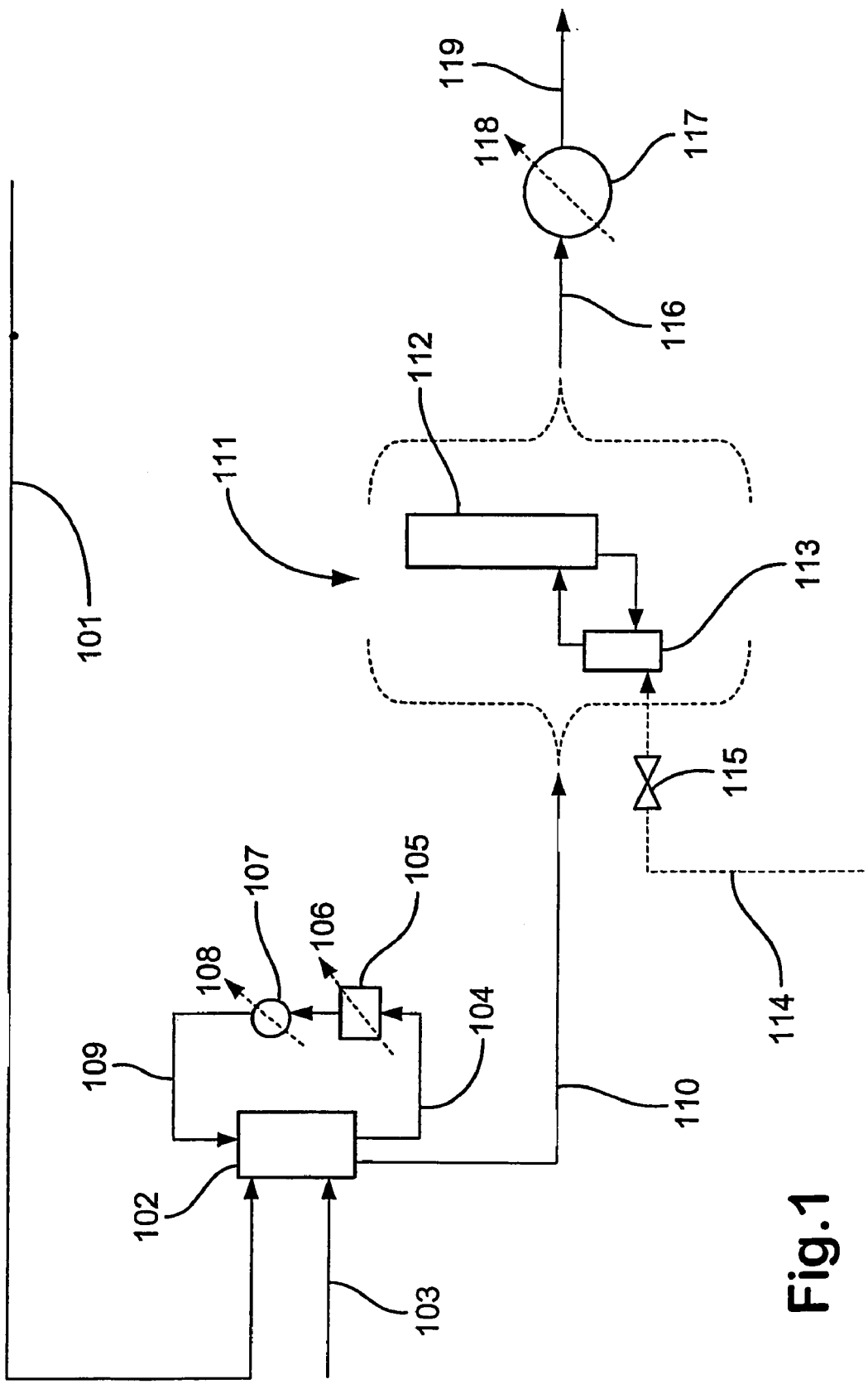
FIG. 1 is a schematic illustration of a process for the carbonylation of methanol to produce acetic acid not according to the present invention.

FIG. 1 is a schematic illustration of a process for the carbonylation of methanol to produce acetic acid. It is not a process according to the present invention as there is no heat transfer from the second heat-exchange stream to a reaction zone feed stream.

Methanol, at a temperature of 20° C., is fed through feed line 101 into reactor 102. Carbon monoxide, at a temperature of 40° C., is fed into the reactor 102 through feed line 103. Within the reactor, there is maintained a liquid reaction composition comprising methanol, iridium catalyst, water, acetic acid and methyl acetate. A first product stream at a temperature of 190° C. is withdrawn from the reactor through lines 104 and 110. The contents of line 104 are fed through heat exchanger 105, wherein heat is transferred to a low pressure steam supply line 106 (first heat-exchange stream) at a pressure of between 5 and 6 barg (0.6 to 0.7 MPa) and a temperature before heat transfer of 150° C. The consequently cooled liquid reaction composition is further cooled in heat exchanger 107 by heat exchange with a cooling water supply line 108, and returned to reactor 102 through line 109.

A second product stream, also at 190° C., is withdrawn from the reactor 102 through line 110 and fed to a flash separation zone (not shown), the vapour fraction from which is fed to a distillation zone 111 comprising one or more distillation columns 112, each having a reboiler 113. One of the reboilers 113 is heated by a supply of medium pressure steam 114 at a pressure of 13 barg and a temperature of 190° C. The flow rate of steam to reboiler 113 is controlled by valve 115. Purified acetic acid at a temperature of 130° C. is withdrawn from the purification zone through line 116 and cooled in heat exchanger 117 with a supply of cooling water 118. The cooled purified acetic acid stream at a temperature of 30° C. is then transferred to storage through line 119.

Figure 2:
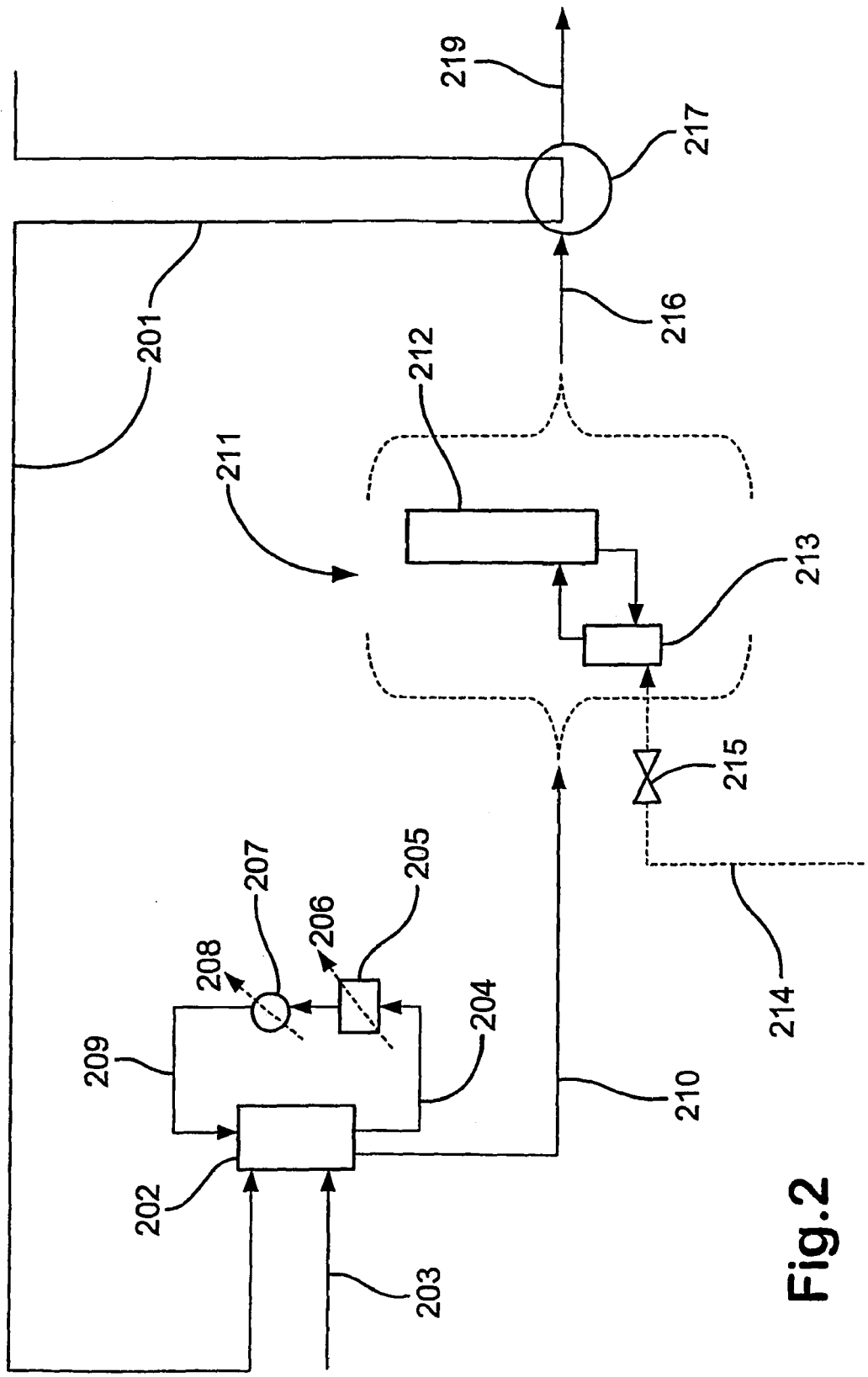
FIGS. 2 and 3 are schematic illustrations of processes for the carbonylation of methanol to produce acetic acid which are in accordance with the present invention.

FIG. 2 is a schematic illustration of a process according to the present invention.

Methanol is fed to reactor 202 through feed line 201 via heat exchanger 217, wherein the temperature of the methanol is raised from 20° C. to 100° C. Carbon monoxide at a temperature of 40° C. is also fed into reactor 202 through feed line 203. Within the reactor, there is maintained a liquid reaction composition comprising methanol, iridium catalyst, water, acetic acid and methyl acetate. A first product stream at a temperature of 190° C. is withdrawn from the reactor through lines 204 and 210. The contents of line 204 are fed through heat exchanger 205, wherein heat is transferred to a low pressure steam supply line 206 (first heat-exchange stream) at a pressure of between 5 and 6 barg (0.6 to 0.7 MPa) and a temperature before heat transfer of 150° C. The consequently cooled liquid reaction composition is further cooled in heat exchanger 207 by heat exchange with a cooling water supply line 208, and returned to reactor 202 through line 209.

A second product stream is withdrawn from the reactor 202 through line 210 and fed to a flash separation zone (not shown), the vapour fraction from which is fed to a distillation zone 211 comprising one or more distillation columns 212, each having a reboiler 213. One of the reboilers 213 is heated by a supply of medium pressure steam 214 at a pressure of 13 barg and a temperature of 190° C. The flow rate of steam to reboiler 213 is controlled by valve 215. Purified acetic acid (second heat-exchange stream) at a temperature of 130° C. is withdrawn from the purification zone through line 216 and cooled in heat exchanger 217 by heat transfer to methanol feed line 201. The cooled purified acetic acid stream at a temperature of 30° C. is then transferred to storage through line 219.

The temperature of any product stream removed from the reactor is maintained at 190° C. by controlling the quantity of heat transferred to the low pressure steam supply line 206 in heat exchanger 205. By such means, the additional heat contained within the hotter methanol stream 201 fed to the reactor is removed by heat exchanger 205 in order to maintain the withdrawn liquid reaction composition at 190° C. In this embodiment of the invention, between 1 and 2 MW of additional heat is transferred to the low pressure steam in line 206 (first heat-exchange stream) compared to the heat transferred to line 106 in the process illustrated in FIG. 1, in which there is no pre-heating of the methanol feed by the purified acetic-acid product line.

Figure 3:
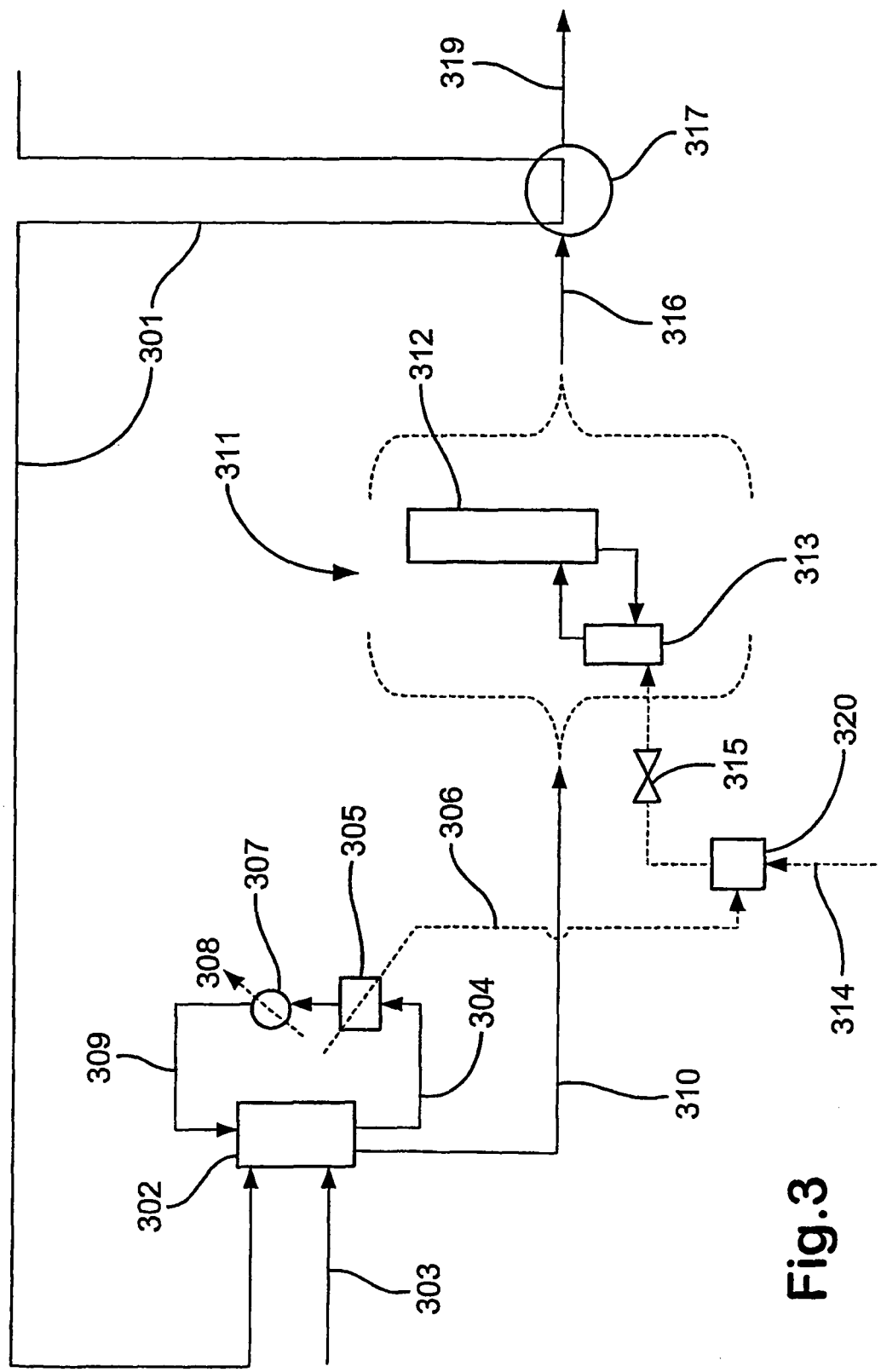

FIG. 3 is a schematic illustration of another process according to the present invention. Methanol is fed to reactor 302 through feed line 301 via heat exchanger 317, wherein the temperature of the methanol is raised from 20° C. to 100° C. Carbon monoxide at a temperature of 40° C. is also fed into reactor 302 through feed line 303. Within the reactor, there is maintained a liquid reaction composition comprising methanol, iridium catalyst, water, acetic acid and methyl acetate. A first product stream at a temperature of 190° C. is withdrawn from the reactor through lines 304 and 310. The contents of line 304 are fed through heat exchanger 305, wherein heat is transferred to a low pressure steam supply line 306 (first-heat exchange stream) at a pressure of between 5 and 6 barg (0.6 to 0.7 MPa) and a temperature before heat transfer of 150° C. The consequently cooled liquid reaction composition is then further cooled in heat exchanger 307 by heat exchange with a cooling water supply line 308, and returned to reactor 302 through line 309.

A second product stream is withdrawn from the reactor 302 through line 310 and fed to a flash separation zone (not shown), the vapour fraction from which is fed to a distillation zone 311 comprising one or more distillation columns 312, each having a reboiler 313. In this embodiment of the invention, at least one of the reboilers is heated by a source of steam derived from a combination of the heated low pressure steam in line 306 (first heat-exchange stream) and a source of medium pressure steam in line 314, which medium pressure steam has a temperature of 190° C. and a pressure of 13 barg before being mixed with the lower pressure steam of line 306 in heat pump 320 to provide steam with a pressure of 10 barg (1.1 MPa). The rate of flow of the mixed steam to the reboiler is controlled through valve 315, which is opened to a greater extent than the valves 115 and 215 of the processes illustrated in FIGS. 1 and 2 respectively.

Purified acetic acid at a temperature of 130° C. is withdrawn from the purification zone through line 316 (second heat-exchange stream) and cooled in heat exchanger 317 by heat transfer to the methanol feed line 301. The cooled purified acetic acid stream at a temperature of 30° C. is then transferred to storage through line 319.

The temperature of liquid reaction composition withdrawn from the reactor is maintained at 190° C. by controlling the quantity of heat transferred to the low pressure steam supply line 306 in heat exchanger 305. Thus, if a hotter feed is fed to the reactor, more heat is removed by heat exchanger 305 in order to maintain the withdrawn liquid reaction composition at 190° C. In this embodiment of the invention, between 1 and 2 MW of additional heat is transferred to the low pressure steam in line 306 (first heat-exchange stream) compared to the heat transferred to line 106 in the process illustrated in FIG. 1, in which there is no pre-heating of the methanol feed by the purified acetic acid product line. As this additionally heated low pressure steam is mixed with medium pressure steam for heating a feed stream to one of the distillation columns in the purification zone, the usage of medium pressure steam is 1 to 2 MW lower than in the examples illustrated in FIGS. 1 and 2.

The invention claimed is:

1. A process for the carbonylation of an alcohol and/or reactive derivative thereof, which process comprises;
   (a) feeding one or more reaction zone feed streams to a reaction zone, wherein at least one reaction zone feed stream comprises an alcohol and/or reactive derivative thereof, and at least one reaction zone feed stream comprises carbon monoxide;
   (b) maintaining in the reaction zone a temperature and pressure sufficient to allow an exothermic carbonylation reaction to take place to produce a carboxylic acid and/or carboxylic acid anhydride;
   (c) removing one or more product streams comprising carboxylic acid and/or carboxylic acid anhydride from the reaction zone; and
   (d) transferring heat contained in at least a portion of the one or more product streams to a first heat-exchange stream;
   wherein heat is transferred from a second heat-exchange stream to a reaction zone feed stream of step (a) before the reaction zone feed stream is fed to the reaction zone, and wherein the temperature of the second heat-exchange stream before heat transfer is lower than that of the one or more product streams.

2. A process as claimed in claim 1, in which the temperature of the second heat-exchange stream before heat transfer to a reaction zone feed stream is lower than that of the first heat-exchange stream before the heat transfer of step (d).

3. A process as claimed in claim 1, in which the second heat-exchange stream before heat transfer to a reaction zone feed stream is below 150° C.

4. A process as claimed in claim 1, in which the first heat-exchange stream is a supply of pressurised steam.

5. A process as claimed in claim 4, in which the supply of pressurised steam has a pressure of up to 0.7 MPa.

6. A process as claimed in claim 1, in which the reaction zone feed stream of step (a) is a liquid stream.

7. A process as claimed in claim 1, in which the reaction zone feed stream to which heat is transferred from the second heat-exchange stream comprises alcohol and/or reactive derivative thereof.

8. A process as claimed in claim 1, in which any product stream or portion thereof from which heat is transferred to the first heat-exchange stream in step (d) is returned to the reaction zone after the heat transfer.

9. A process as claimed in claim 1, in which the temperature of the reaction zone feed stream is 80° C. or below before heat is transferred from the second heat-exchange stream.

10. A process as claimed in claim 1, in which at least a portion of the one or more product streams is fed to a purification zone, and the second heat-exchange stream is a process stream of the purification zone.

11. A process as claimed in claim 10, in which the second heat-exchange stream is a purified carboxylic acid and/or carboxylic anhydride product stream of the purification zone.

12. A process as claimed in claim 1, in which the process is homogeneously catalysed and there is maintained in the reaction zone a liquid reaction composition comprising alcohol and/or reactive derivative thereof, carboxylic acid and/or carboxylic acid anhydride, and a group VIII carbonylation catalyst.

13. A process as claimed in claim 12, in which the group VIII carbonylation catalyst is selected from rhodium and/or iridium.

14. A process as claimed in claim 12, in which the purification zone comprises a flash separation zone and a distillation zone, wherein least a portion of the one or more product streams is fed to the flash separation zone to produce a liquid fraction comprising group VIII carbonylation catalyst and a vapour fraction comprising carboxylic acid and/or carboxylic acid anhydride, in which the liquid fraction is returned to the reactor and the vapour fraction is fed to the distillation zone to produce purified carboxylic acid and/or carboxylic acid anhydride.

15. A process as claimed in claim 1, in which the alcohol and or reactive derivative thereof is methanol and/or reactive derivative thereof, and the product is acetic acid.

16. A process as claimed in claim 1, in which the reaction zone is maintained at a temperature in the range of from 100 to 300° C., and a pressure of from 1.7 to 10.0 MPa.

* * * * *